US008426335B2

United States Patent
Yunoki et al.

(10) Patent No.: US 8,426,335 B2
(45) Date of Patent: Apr. 23, 2013

(54) CATALYST AND PROCESS FOR PRODUCTION OF ACRYLIC ACID

(75) Inventors: Hiromi Yunoki, Himeji (JP); Michio Tanimoto, Himeji (JP); Daisuke Nakamura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/287,082

(22) Filed: Oct. 6, 2008

(65) Prior Publication Data

US 2009/0043128 A1 Feb. 12, 2009

Related U.S. Application Data

(62) Division of application No. 11/212,474, filed on Aug. 26, 2005, now abandoned.

(51) Int. Cl.
*C01B 15/16* (2006.01)
*C01B 25/26* (2006.01)
*C01B 25/16* (2006.01)
*C07C 51/16* (2006.01)
*C07C 51/235* (2006.01)

(52) U.S. Cl.
USPC ........... 502/312; 502/305; 502/311; 502/321; 562/532; 562/533; 562/535

(58) Field of Classification Search .......... 502/305–323; 568/532–549
See application file for complete search history.

(56) References Cited

U.S. PATENT DOCUMENTS

| | | | |
|---|---|---|---|
| 4,251,393 A | 2/1981 | Dalton et al. | |
| 4,297,247 A | 10/1981 | Krabetz et al. | |
| 4,442,308 A | 4/1984 | Arntz et al. | |
| 4,873,217 A | 10/1989 | Kawajiri et al. | |
| 5,446,004 A | 8/1995 | Tenten et al. | |
| 5,493,052 A | 2/1996 | Tenten et al. | |
| 5,677,261 A | 10/1997 | Tenten et al. | |
| 5,723,403 A | 3/1998 | Durand et al. | |
| 5,959,143 A | 9/1999 | Sugi et al. | |
| 6,303,537 B1 | 10/2001 | Wang et al. | |
| 6,753,291 B2 | 6/2004 | Eijsbouts et al. | |
| 6,762,148 B2 | 7/2004 | Ohishi et al. | |
| 6,821,923 B1 | 11/2004 | Kuperman et al. | |
| 6,960,684 B2 * | 11/2005 | Yunoki | 562/547 |
| 7,022,643 B2 | 4/2006 | Yunoki et al. | |
| 2004/0058812 A1 | 3/2004 | Yunoki et al. | |
| 2006/0063951 A1 | 3/2006 | Yunoki et al. | |

FOREIGN PATENT DOCUMENTS

| | | |
|---|---|---|
| DE | 196 23 413 A1 | 12/1997 |
| EP | 0 017 000 A1 | 10/1980 |
| EP | 0 293 859 A1 | 12/1988 |
| EP | 0 807 465 A1 | 11/1997 |
| FR | 2 750 619 A1 | 1/1998 |
| GB | 1 496 832 | 1/1978 |
| JP | 57-3415 B2 | 1/1982 |
| JP | 57-110338 A | 7/1982 |
| JP | 58-930 A | 1/1983 |
| JP | 58-15176 B2 | 3/1983 |
| JP | 63-315147 A | 12/1988 |
| JP | 64-58336 A | 3/1989 |
| JP | 5-96183 A | 4/1993 |
| JP | 5-42295 B2 | 6/1993 |
| JP | 6-31171 A | 2/1994 |
| JP | 6-279030 A | 10/1994 |
| JP | 8-10621 A | 1/1996 |
| JP | 8-252464 A | 10/1996 |
| JP | 8-299797 A | 11/1996 |
| JP | 10-192675 A | 7/1998 |
| JP | 2000-355571 A | 12/2000 |
| JP | 2001-79408 A | 3/2001 |
| JP | 2002-282696 A | 10/2002 |
| JP | 2004-136267 A | 5/2004 |

OTHER PUBLICATIONS

The Society of Chemical Engineers—Japan, Collected Summaries of Research Results Presentation Lectures at 53rd Annual Meeting of the Society of Chemical Engineers—Japan, 1988, p. 128 (C310), No. I, The Society of Chemical Engineers—Japan, Japan.

* cited by examiner

*Primary Examiner* — Kaj K Olsen
*Assistant Examiner* — Jennifer Smith

(57) ABSTRACT

An object of the present invention is to provide: a catalyst for production of acrylic acid which is a catalyst usable for production of acrylic acid and is excellent in the catalytic performances such as catalytic activity and in the physical properties such as physical strength of the catalyst itself; and a process for production of acrylic acid using this catalyst. As a means of achieving this object, a catalyst for production of acrylic acid according to the present invention is a catalyst obtained by drying a mixed liquid of starting materials including molybdenum and vanadium as essential components to give a dried material, molding the dried material with a liquid binder, and calcining the resultant molding, with the catalyst being characterized in that an ignition loss ratio of the dried material is from 5 to 40% by mass. A process for production of acrylic acid according to the present invention comprises the step of: subjecting acrolein to a catalytic gas phase oxidation in the presence of a molecular oxygen, with the process being characterized in that the above catalyst for production of acrylic acid according to the present invention is used.

12 Claims, No Drawings

US 8,426,335 B2

CATALYST AND PROCESS FOR PRODUCTION OF ACRYLIC ACID

This is a divisional of U.S. patent application Ser. No. 11/212,474 filed Aug. 26, 2005 and claims the benefit thereof under 35 U.S.C. §120.

BACKGROUND OF THE INVENTION

A. Technical Field

The present invention relates to a catalyst used for production of acrylic acid and a process for production of acrylic acid using this catalyst. Specifically, the present invention relates to: a catalyst for production of acrylic acid, which catalyst is excellent in activity, selectivity, and physical strength and the like; and a process for production of acrylic acid by subjecting acrolein to catalytic gas phase oxidation in the presence of molecular oxygen and the catalyst.

B. Background Art

As a catalyst for efficiently producing acrylic acid by catalytic gas phase oxidation of acrolein (catalyst for production of acrylic acid), there is often used a catalyst which is obtained by a process comprising the steps of: adding a liquid binder to a powder obtained from a mixed liquid of starting materials including molybdenum and vanadium as essential components; molding the resultant mixture; and then calcining the resultant molding. As to processes for producing this catalyst, various proposals have been made.

Examples of these production processes include: (1) a process comprising the steps of evaporating a mixed liquid of starting materials to dryness, adding polyvinyl alcohol, a water-absorbent resin, and water to the resultant dried powder, and then kneading and extruding the resultant mixture (for example, see patent document 1 below); (2) a process comprising the steps of spraywise drying a mixed liquid of starting materials and calcining at 400° C., and then supporting the resultant calcined mixture onto a carrier using water as a binder by a rotating drum type supporting apparatus (for example, see patent document 2 below); (3) a process comprising the steps of drying a mixed liquid of starting materials by any method of evaporation to dryness, spray drying, drum drying, and gas flow drying, calcining the resultant dried powder, and then adding propyl alcohol and water to the resultant calcined material, mixing, and then extruding the resultant mixture (for example, see patent document 3 below); (4) a process comprising the steps of spraywise drying a mixed liquid of starting materials and calcining at 400° C., and then supporting the resultant calcined mixture onto a carrier using a liquid binder including water and an organic compound having a boiling point or sublimation temperature of higher than 100° C. under normal pressure (for example, see patent document 4 below); and (5) a process comprising the steps of drying a mixed liquid of starting materials and pre-calcining at a temperature in the range of 250 to 500° C., and then supporting the resultant calcined mixture onto a carrier using such as an aqueous glycerol solution as a binder by a tumbling granulator (for example, see patent document 5 and patent document 6 below).

[Patent Document 1]
JP-A-096183/1993 (Kokai)
[Patent Document 2]
JP-A-279030/1994 (Kokai)
[Patent Document 3]
JP-A-010621/1996 (Kokai)
[Patent Document 4]
JP-A-252464/1996 (Kokai)
[Patent Document 5]
JP-A-299797/1996 (Kokai)
[Patent Document 6]
JP-A-079408/2001 (Kokai)

However, all the catalysts for production of acrylic acid, which catalysts are obtained by the above prior processes, are still insufficient in the catalytic performances such as catalytic activity and in the physical strength of the catalysts themselves.

SUMMARY OF THE INVENTION

A. Object of the Invention

An object of the present invention is therefore to provide: a catalyst for production of acrylic acid which is a catalyst usable for production of acrylic acid and is excellent in the catalytic performances such as catalytic activity and in the physical properties such as physical strength of the catalyst itself; and a process for production of acrylic acid using this catalyst.

B. Disclosure of the Invention

The present inventors diligently studied to solve the above-mentioned problems.

As a result, the present inventors have noticed that it is a good idea to direct their attention to a specific property concerning a dried material of a mixed liquid of starting materials used for preparing a catalyst (specifically, used in the step of molding a catalyst). Specifically, the present inventors have found that as focusing on a physical property aspect referred to as the below-defined "ignition loss ratio" (which has never been assessed hitherto) upon heating the above dried material to constant mass (until there is no change in mass), if a new non-conventional dried material which, when heated under specific conditions, loses its mass and exhibits a value of the above ignition loss ratio satisfying a specific range is used as the above dried material, then a catalyst for production of acrylic acid can be obtained wherein this catalyst can solve the above-mentioned problems all at once and easily.

The present inventors have also found that as focusing on a physical property aspect referred to as the below-defined "attrition loss" of the resultant catalyst for production of acrylic acid, a new non-conventional catalyst having a value satisfying a specific range of the attrition loss can solve the above-mentioned problems all at once and easily.

And then the present inventors have further confirmed that acrylic acid can efficiently be obtained as a result of actually using the above catalyst for production of acrylic acid in the catalytic gas phase oxidation of acrolein, and have thus completed the present invention.

That is to say, a catalyst for production of acrylic acid according to the present invention is a catalyst obtained by drying a mixed liquid of starting materials including molybdenum and vanadium as essential components to give a dried material, molding the dried material with a liquid binder, and calcining the resultant molding, with the catalyst being characterized in that an ignition loss ratio of the dried material is from 5 to 40% by mass, with the proviso that the above ignition loss ratio is calculated according to the following formula based on masses of the dried material before and after heated, the dried material being heated until there is no mass change at 300° C. under air atmosphere:

ignition loss ratio(% by mass)=[(mass of dried material before heated(g)−mass of dried material after heated(g))/mass of dried material before heated (g)]×100.

In addition, another catalyst for production of acrylic acid according to the present invention is a catalyst obtained by drying a mixed liquid of starting materials including molybdenum and vanadium as essential components to give a dried material, molding the dried material with a liquid binder, and calcining the resultant molding, with the catalyst being characterized in that an attrition loss of the catalyst is less than 10% by mass, with the proviso that the attrition loss is calculated according to the following formula based on a mass (g) of the resultant catalyst for production of acrylic acid initially charged into a stainless airtight vessel, which is in the form of a cylindrical drum of 150 mm diameter of circular section in perpendicular direction and 150 mm width in horizontal direction, and a mass (g) of the catalyst remaining on a 2.0 mm-mesh sieve after subjected to an operation comprising the steps of weighing out 200±1 g of the catalyst precisely, charging the weighed catalyst into the stainless airtight vessel, rotating the vessel for 30 minutes at 150 rpm around a horizontal central axis thereof, and then putting the catalyst through the sieve:

attrition loss(% by mass)=[(mass of catalyst initially charged into vessel(g)−mass of catalyst remaining on sieve(g))/mass of catalyst initially charged into vessel(g)]×100.

In addition, a process for production of acrylic acid according to the present invention comprises the step of: subjecting acrolein to a catalytic gas phase oxidation in the presence of a molecular oxygen, with the process being characterized in that the above catalyst for production of acrylic acid according to the present invention is used.

DETAILED DESCRIPTION OF THE INVENTION

Hereinafter, detailed descriptions are given about the catalyst for production of acrylic acid according to the present invention and the process for production of acrylic acid using this catalyst. However, the scope of the present invention is not bound to these descriptions. And other than the following illustrations can also be carried out in the form of appropriate modifications of the following illustrations within the scope not departing from the spirit of the present invention.

The catalyst for production of acrylic acid according to the present invention is obtained by a process comprising the steps of: (1) drying a mixed liquid (which is in a state of an aqueous solution or slurry) of starting materials including molybdenum and vanadium as essential components to obtain a dried material; (2) molding the dried material with a liquid binder; and (3) calcining the resultant molding, wherein the dried material obtained in the above step (1) is made to have the previously defined ignition loss ratio (detail is described below) of 5 to 40% by mass, and/or the resultant catalyst for production of acrylic acid is made to have the attrition loss (detail is described below) of less than 10% by mass.

The catalyst for production of acrylic acid according to the present invention can be any catalyst as long as it comprises an oxide and/or a composite oxide including molybdenum and vanadium as essential metal elements and enables the production of acrylic acid from acrolein by its catalytic gas phase oxidation reaction. However, it is preferable that the oxide and/or composite oxide comprising molybdenum and vanadium as essential metal elements is an oxide and/or composite oxide having a metal element composition represented by the following general formula (I):

$$Mo_aV_bA_cB_dC_eO_x \quad (1)$$

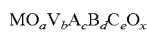

(wherein: Mo is molybdenum; V is vanadium; A is niobium and/or tungsten; B is at least one element selected from the group consisting of chromium, manganese, iron, cobalt, nickel, copper, zinc, and bismuth; C is at least one element selected from the group consisting of tin, antimony, and tellurium; O is oxygen; and a, b, c, d, e, and x denote atomic ratios of Mo, V, A, B, C, and O respectively, wherein: when a=12, the following are satisfied: $1 \leq b \leq 14$; $0 < c \leq 12$; $0 < d \leq 10$; and $0 \leq e \leq 10$; and x is a numerical value as determined by the oxidation state of each element).

There is no special limitation on the starting materials for obtaining the above oxide and/or composite oxide comprising molybdenum and vanadium as essential metal elements. Ammonium salts, nitrates, carbonates, chlorides, sulfates, hydroxides, organic acid salts, and oxides of metal elements which are generally used for this kind of catalyst, or a mixture thereof, may be used in combination of a plurality of them. Preferably, the ammonium salts and the nitrates are used.

The mixed liquid of the starting materials (starting-materials-mixed liquid) may be prepared by processes as generally used for production of this kind of catalyst. For example, the above starting materials are added into water in order, thereby forming an aqueous solution or slurry. In the case where a plurality of aqueous solutions or slurries are prepared according to the kinds of the starting materials, these aqueous solutions or slurries may be mixed together in order. There is no special limitation on the conditions for the above mixing (e.g. mixing order, temperature, pressure, and pH).

To obtain a dried material from the resultant mixed liquid of the starting materials, the mixed liquid of the starting materials is dried by various methods. Examples of these methods include drying methods by heating and drying methods under reduced pressure.

The dried material is substantially free from water, but it is enough for the dried material to be in a solid state to such a degree that it can be formed into a powder. Accordingly, some water may remain according to the drying conditions and the like.

As to the heating method for obtaining the dried material and as to the form of the resultant dried material, for example, a powdery dried material may be obtained with such as a spray dryer and a drum dryer, or a blockish or flaky dried material may be obtained by heating under a gas stream with such as a box-type dryer or a tunnel-type dryer. Incidentally, in the above-mentioned heating method, the heating period (the period of time when heat is applied to the mixed liquid of the starting materials) is preferably a short time (for example, from several seconds to tens of minutes). Gradual drying by heating for a long time (for example, several hours (at least 2 to 3 hours)) such as evaporation-to-dryness method is undesirable because the dried material having the specific physical properties according to the present invention cannot be obtained.

The above-mentioned heating conditions such as heating temperature and heating period upon preparing the dried material should be appropriately selected according to the kind and feature of a heating apparatus (e.g. a drier) and cannot sweepingly be specified. However, for example, the heating temperature is preferably not more than 230° C. and the heating period is preferably less than 90 minutes, and more preferably less than 30 minutes.

On the other hand, as to the method of drying under reduced pressure and as to the form of the resultant dried material, for example a vacuum drier may be used to obtain a blockish or powdery dried material.

In the present invention, it is important that the ignition loss ratio of the dried material is 5 to 40% by mass, which is preferably 10 to 35% by mass, and more preferably 15 to 30% by mass. For example, the above heating (heating upon preparation of the dried material) conditions are appropriately set so that the ignition loss ratio of the dried material will satisfy the above specific range. When the ignition loss ratio of the dried material is above 40% by mass, a dried material may be prepared again by a change of conditions such as a change of temperature of heating gas upon preparation of the dried material so as to have an ignition loss ratio value satisfying the above specific range. Alternatively, it is also possible that: at the preparation stage of the mixed liquid of the starting materials or before molding the once-obtained dried material or supporting it onto a carrier, an appropriate amount of material (for example, ammonium nitrate) that can be decomposed and removed from the dried material under the measurement condition of the ignition loss ratio, namely, "heating at 300° C. under air atmosphere", is added to the mixed liquid of the starting materials or to the dried material, whereby the dried material is provided with an ignition loss ratio satisfying the above specific range.

In the present invention, when the ignition loss ratio of the dried material satisfies the above specific range, a catalyst for production of acrylic acid can be obtained which catalyst is excellent in such as physical strength of the catalyst itself, and so excellent in catalytic performances such as catalytic activity that acrylic acid can be efficiently produced when the catalyst is used in the reaction system producing acrylic acid by catalytic gas phase oxidation of acrolein. If the ignition loss ratio of the dried material is less than 5% by mass, there is a possibility that: as to the resultant catalyst for production of acrylic acid, the catalytic performances such as catalytic activity may be inferior, and the yield of the objective product acrylic acid may also be low, and the physical strength of the catalyst itself may be inferior. On the other hand, if the ignition loss ratio is more than 40% by mass, there is a possibility as follows. Due to rapid decomposition of the starting materials such as nitrate and ammonium salt in heating (for example, calcining) after molding, the resultant catalyst for production of acrylic acid may be much inferior in physical strength of the catalyst itself and further in moldability of the dried material in the process of producing the catalyst, so that every catalyst may be deformed and therefore no catalyst of a desired shape cannot be obtained. Furthermore, for example, in the case of molding by an extrusion-molding machine, the viscosity of the dried material may increase more than necessary upon compression and thus the molding rate may greatly decrease, so that, when things come to the worst, the dried material cannot be molded. In addition, in the case of molding by a tumbling granulator, the viscosity of the dried material may increase during the granulating operation, so that granulated particles may cohere to aggregate. Furthermore, in the case of preparing a supported catalyst, a large amount of the dried material may attach to the inner surface of a supporting vessel, thus resulting in a low yield.

In the present invention, the ignition loss ratio of the dried material is a value calculated from weighing results before and after heating the dried material of the mixed liquid of the starting materials under the specific conditions and from the following calculation formula. Specifically, 10 g of the dried material obtained from the mixed liquid of the starting materials is weighed out precisely and heated at 300° C. under air atmosphere until there is no change in mass, and then the ignition loss ratio is calculated according to the following formula based on masses of the dried material before and after the above heating:

ignition loss ratio(% by mass)=[(mass of dried material before heated(g)−mass of dried material after heated(g))/mass of dried material before heated(g)]×100.

The heating period for obtaining the ignition loss ratio may be at least a period of time from the start of the above heating until there is no change in mass of the dried material as described above, and the above heating period may be extended to a stage after there is no change in mass. Incidentally, usually, if the above heating period is set not to be less than 1 hour, then it is possible to put the dried material in a state where there is no change in mass of the dried material.

The ignition loss ratio of the dried material can be adjusted in a way that: for example, in the case of heating for obtaining the dried material by using a box-type dryer, the temperature of the heating gas and/or the linear velocity of the heating gas and/or the heating period is appropriately adjusted. The higher the temperature of the heating gas is and the higher the linear velocity of the heating gas is and the longer the heating period is, then the smaller the ignition loss ratio of the dried material can be made. Specifically, for example, in the case of heating for obtaining the dried material with a drum drier, the ignition loss ratio can be adjusted by appropriately controlling the contacting period of the catalytic ingredients with the surface of the drum or the drum temperature (steam pressure when the drum heating method is steam heating).

The losses upon measuring the ignition loss ratio are those which are decomposed, volatilized or sublimated by heating upon measuring the ignition loss ratio, and include such as nitrate radical and ammonium radical still remaining in the prepared dried material (for example, those which are originated from the starting materials or have been added separately therefrom). In some cases, there is also included such as water remaining after the preparation of the dried material (Nitrate and ammonium salt and the like contained in the dried material are decomposed by heating at high temperature and thereby removed from the dried material. In other words, a dried material having a higher ignition loss ratio means that it contains the above nitrate and ammonium salt and the like in a higher proportion).

The dried material obtained by adjusting the ignition loss ratio in the specific range in the above way is fed to the subsequent molding step after, as needed, subjected to the pulverizing and/or classifying step for obtaining a powder of an appropriate particle size. Incidentally, the above particle size of the powder of the dried material is not specially limited. However, it is preferably not more than 500 μm. In addition, in the present invention, it is important to actually use a dried material itself of an ignition loss ratio satisfying the specific range to mold a catalyst. For example, even if, for molding a catalyst, there is used a dried material obtained by a process in which the above specific dried material has once been prepared for using it to mold a catalyst, but thereafter its ignition loss ratio has come not to satisfy the specific range as a result of a further treatment such as calcining before molding, then it can't solve the above-described problems.

In the molding step, the liquid binder and the like can be used for molding (including supporting onto a carrier) the dried material which is a precursor of catalytic ingredients. Specifically, there can be employed such as a method including the steps of adding the liquid binder to the resultant dried material, mixing them together and then molding the resultant mixture; or, in the case of supporting the resultant dried material onto a desired carrier (i.e. obtaining a supported catalyst), a method including the steps of wetting the carrier with the liquid binder and then adding the dried material to the wetted carrier to support the dried material onto the carrier. As to the liquid binder, for example, any kind of already publicly known liquid binder which usually can be used for molding a catalyst can be used without special limitation, but an aqueous binder or aqueous binder solution is preferably used, and water is more preferably used.

When using the aqueous binder or aqueous binder solution among the above liquid binders, the amount used is not specially limited, yet it is preferably 2 to 20 parts by mass, more preferably 3 to 17 parts by mass, and still more preferably 4 to 14 parts by mass, in terms of water relative to 100 parts by mass of the dried material. If the amount used is more than 20 parts by mass, there is a possibility that the moldability of the dried material may be deteriorated, thus resulting in failure to mold the dried material. If the amount used is less than 2 parts by mass, there is a possibility that: the molding itself of the dried material may be impossible due to its weak bonding to each other, or the physical strength of the resultant catalyst may be inferior even if the dried material can be molded.

The above liquid binder is usable also in the form as obtained by adding thereto aqueous solutions of various substances and/or the various substances alone and mixing them together. Examples of the various substances include: molding assistants for enhancing the moldability; reinforcements and binders for enhancing the catalyst strength; and substances that are commonly used as pore-forming agents for formation of pores in the catalyst. Preferable substances are those having no bad influence on the catalytic performances (e.g.: activity; selectivity of aimed product) by addition of them. Specifically, the preferable substances are, for example, as follows: (1) substances that do not remain in the catalyst after calcination; and (2) substances that do not have bad influence on the catalytic performances even if they remain in the catalyst after calcination.

Specific examples of the substances (1) include an organic compound such as ethylene glycol, glycerol, propionic acid, maleic acid, benzyl alcohol, propyl alcohol, butyl alcohol or phenol, and nitric acid, ammonium nitrate, ammonium carbonate and the like.

Specific examples of the substances (2) include those commonly known as the reinforcement, such as silica, alumina, glass fibers, silicon carbide, and silicon nitride. The catalyst produced according to the present invention has a practically sufficient physical strength, but these reinforcements are added thereto when a still higher physical strength is necessary.

When the amount of these various substances added is in excess, the physical strength of the catalyst is remarkably decreased. Therefore it is desirable to add them in such an amount as does not reduce the physical strength of the catalyst to such an extent that the catalyst cannot be practically used as an industrial catalyst.

When adding the liquid binder in the form of the above mixture of water with the aqueous solutions of the various substances or with these various substances, for example, in the case of adding 20 parts by mass of a 5% by mass aqueous ethylene glycol solution to 100 parts by mass of the dried material and molding the resultant mixture, the amount of water added to the dried material is calculated as 19 parts by mass from $20 \times (1-0.05)$.

The catalyst for production of acrylic acid according to the present invention may be a molded type catalyst obtained by molding the dried material into a definite shape, or may be a supported type catalyst molded by supporting (obtained by supporting) the dried material onto any inert carrier having a definite shape.

In the case of the supported type catalyst, the supporting ratio of the catalyst is appropriately determined in consideration of oxidation reaction conditions, activity and strength of the catalyst, and the like, but is preferably in the range of 10 to 70% by mass, more favorably 15 to 50% by mass. The supporting ratio is defined as a value determined by the calculation method described in the below-mentioned "DETAILED DESCRIPTION OF THE PREFERRED EMBODIMENTS" section hereof.

In the case of the supported type catalyst, examples of the inert carrier include alumina, silica, silica-alumina, titania, magnesia, steatite, silica-magnesia, silicon carbide, silicon nitride and zeolite.

The method for molding the catalyst may be an already publicly known method. Applicable are, for example, molding methods such as extrusion-molding methods (extrusion-molding machines), granulation methods (tumbling granulators and centrifugal-flow-coating apparatus), and Marumerizer method.

The shape of the catalyst for production of acrylic acid according to the present invention is not specifically limited. For example, any shape such as a column shape, a ring shape, a spherical shape, and an irregular shape can be selected.

The average diameter of the catalyst for production of acrylic acid according to the present invention is from 3 to 15 mm, preferably 4 to 10 mm.

When obtaining the catalyst for production of acrylic acid according to the present invention by a process comprising the steps of molding the dried material with such as the liquid binder and then calcining the resultant molding, the calcining temperature is preferably 350 to 450° C., and more preferably 380° C. to 420° C., and the calcining period is preferably about 1 to about 10 hours. Before being calcined, the above molding may be heat-treated at a temperature lower than the calcination temperature.

In the present invention, it is important to make the attrition loss of the resultant catalyst for production of acrylic acid less than 10% by mass, which is preferably less than 7% by mass, and more preferably less than 5% by mass. To make the attrition loss of the catalyst satisfy the above specific range, for example, it will do to use a dried material having the previously explained ignition loss ratio of 5 to 40% by mass (preferably 10 to 35% by mass, and more preferably 15 to 30% by mass) for preparation of the catalyst. Additionally, it is desirable to use an aqueous binder or aqueous binder solution as a liquid binder in an amount of 2 to 20 parts by mass (preferably 3 to 17 parts by mass, and more preferably 4 to 14 parts by mass) in terms of water relative to 100 parts by mass of the dried material.

When using a catalyst having an attrition loss of not less than 10% by mass in the oxidation reaction, such as the following problems may occur. In an operation of filling the catalyst into a reactor, there is commonly adopted a method in which the catalyst is dropped from the top of the reaction tube. However, if the catalyst has an attrition loss of not less than 10% by mass, there is a possibility that: the catalyst itself may be damaged by its collision with each other or with the inner surface of the reaction tube due to the above dropping, so that a part of the catalyst may be chipped or broken; or in the case of the supported type catalyst, much of the catalytic ingredients may peel off from the carrier to thus increase the pressure drop of a catalyst layer after filling the catalyst, so that the yield of the target product may be low when carrying out the oxidation reaction. In addition, there is a possibility that: economical problems may also occur such as an increased cost of power of a blower for introducing a gas to be reacted into the reactor.

In the present invention, the attrition loss of the resultant catalyst is determined as follows. That is, 200±1 g of the resultant catalyst is weighed out precisely and charged into a cylindrical-drum-shaped stainless airtight vessel having a diameter of 150 mm in circular section in perpendicular direction and a width of 150 mm in horizontal direction. This stainless airtight vessel is rotated for 30 minutes at 150 rpm around a horizontal central axis thereof. Then, the catalyst is removed from the stainless airtight vessel and put through a 2.0 mm-mesh sieve, and the mass (g) of the catalyst remaining on the sieve is weighed. Then, the attrition loss is calculated according to the following formula based on a mass (g) of the catalyst initially charged into the stainless airtight vessel, and a mass (g) of the catalyst remaining on the 2.0 mm-mesh sieve:

attrition loss(% by mass)=[(mass of catalyst initially charged into vessel(g)−mass of catalyst remaining on sieve(g))/mass of catalyst initially charged into vessel(g)]×100.

The specific surface area of the catalyst for production of acrylic acid according to the present invention is not specifically limited. However, it is preferably from 5 to 20 $m^2/g$, more preferably 7 to 18 $m^2/g$, and still more preferably 9 to 16 $m^2/g$. If the specific surface area of the catalyst is less than 5 $m^2/g$, there is a possibility that: the catalytic activity may be so insufficient as to result in a low conversion of acrolein. If the specific surface area of the catalyst is more than 20 $m^2/g$, there is a possibility that: the selectivity of acrolein may be decreased. Incidentally, the carrier part is not taken into account when the catalyst according to the present invention is in the form of the above-mentioned supported type catalyst.

As a method for measuring the above specific surface area, there is employed a method in which that of the catalyst for production of acrylic acid obtained after calcination is measured by BET method. Incidentally, when the resultant catalyst for production of acrylic acid is the supported type catalyst, catalytic ingredients supported on the carrier are peeled off therefrom and measured by the BET method.

The method for peeling off the catalytic ingredients is not specifically limited. However, specific examples thereof include: a method in which the supported catalytic ingredients are peeled off from the carrier by shaking an appropriate amount of catalyst for a certain time in a vessel such as glass vessel; and a method in which the supported catalytic ingredients are peeled off from the carrier by using a keen tool such as cutter knife. Examples of devices usable favorably for measuring the above specific surface area include a specific surface area measuring device (Product Name: U2C) manufactured by Yuasa Ionics Inc.

The process for production of acrylic acid according to the present invention comprises the step of: subjecting acrolein to a catalytic gas phase oxidation in the presence of a molecular oxygen, with the process being characterized in that the above catalyst for production of acrylic acid according to the present invention is used.

The process for production of acrylic acid by subjecting acrolein to catalytic gas phase oxidation has no specific limitation, except for using the catalyst according to the present invention as a catalyst, and can be carried out with conventional apparatuses, by conventional methods, and under conventional conditions.

The above acrolein is subjected to the catalytic gas phase oxidation generally in a state of a raw gas containing this acrolein. As such a raw gas, needless to say a mixed gas including acrolein, oxygen, and an inert gas, a mixed gas containing acrolein as obtained by direct oxidation of propylene is also usable after air or oxygen and further water vapor and/or another gas have been added thereto if necessary. Such as acrylic acid, acetic acid, carbon oxide, propane (these are by-products) and unreacted propylene, which are contained in the mixed gas containing acrolein as obtained by direct oxidation of propylene, do no harm upon the catalyst for production of acrylic acid used in the present invention.

The catalytic gas phase oxidation reaction in the present invention may be carried out by either of a one-pass method and a recycling method. Such as fixed-bed reactors, fluidized-bed reactors, and moving-bed reactors can be used as reactors.

As to conditions of the above reaction, conditions as conventionally used for the production of acrylic acid by the catalytic gas phase oxidation reaction can be employed. For example, the reaction may be carried out by bringing a mixed gas into contact with the above catalyst for production of acrylic acid according to the present invention in the temperature range of 200 to 400° C. (preferably 220 to 380° C.) under a pressure of 0.1 to 1 MPa at a space velocity of 300 to 10,000 $hr^{-1}$ (STP) (preferably 500 to 5,000 $hr^{-1}$ (STP)), wherein the mixed gas comprises 1 to 15% by volume (favorably 4 to 12% by volume) of acrolein, 0.5 to 25% by volume (favorably 2 to 20% by volume) of oxygen, 0 to 30% by volume (favorably 0 to 25% by volume) of water vapor, and 20 to 80% by volume (favorably 50 to 70% by volume) of an inert gas such as nitrogen.

EFFECTS AND ADVANTAGES OF THE INVENTION

The present invention can provide: a catalyst for production of acrylic acid which is a catalyst usable for production of acrylic acid and is excellent in the catalytic performances such as catalytic activity and in the physical properties such as physical strength of the catalyst itself; and a process for production of acrylic acid using this catalyst.

DETAILED DESCRIPTION OF THE PREFERRED EMBODIMENTS

Hereinafter, the present invention is more specifically illustrated by the following Examples of some preferred embodiments. However, the present invention is not limited to them in any way. Incidentally, hereinafter, for convenience, the units "part(s) by mass" and "liter(s)" may be referred to simply as "part(s)" and "L" respectively.

The details of various measurement and calculation methods in the following Examples and Comparative Examples are described below.

<Calculation Method of Ignition Loss Ratio of Dried Material>

The details are as described previously, and calculated according to the following formula:

ignition loss ratio(% by mass)=[(mass of dried material before heated(g)−mass of dried material after heated(g))/mass of dried material before heated (g)]×100.

<Calculation Method of Attrition Loss of Catalyst>

The details are as described previously, and calculated according to the following formula:

attrition loss(% by mass)=[(mass of catalyst initially charged into vessel(g)−mass of catalyst remaining on sieve(g))/mass of catalyst initially charged into vessel(g)]×100.

<Calculation Method of Supporting Ratio>

Supporting ratio(% by mass)[(mass of catalyst obtained(g)−mass of carrier used(g))/mass of catalyst obtained(g)]×100

<Conversion of Acrolein>

Conversion of acrolein(% by mol)=(mols of reacted acrolein/mols of supplied acrolein)×100

<Yield of Acrylic Acid>

Yield of acrylic acid(% by mol)=(mols of produced acrylic acid/mols of supplied acrolein)×100

<Selectivity of Acrylic Acid>

Selectivity of acrylic acid(% by mol)=(mols of produced acrylic acid/mols of reacted acrolein)×100

Example 1

Preparation of Dried Material

Ammonium molybdate (3,000 parts), 961 parts of ammonium metavanadate and 612 parts of ammonium paratungstate were dissolved into 20,000 parts of pure water under heating and mixing. Separately from this, 890 parts of copper nitrate trihydrate was dissolved into 2,000 parts of pure water under heating and mixing. The resultant two aqueous solutions were mixed together to obtain a mixed liquid of starting materials.

This mixed liquid of starting materials was sprayed to a drum dryer being heated with a steam of 476 kPa in pressure, thus obtaining a solid. In this step, the contacting period with the surface of the drum (time from spraying the mixed liquid of starting materials to the drum surface of the drum dryer till scraping the resultant solid off from the drum surface; the same in the following Examples and Comparative Examples) was 60 seconds.

Then, this solid was treated by heating for 60 minutes at 220° C. under air atmosphere and then pulverized so as to have particle sizes of not more than 500 μm, thus obtaining a dried material (A).

(Production of Catalyst)

Onto a rotating dish of a dish type tumbling granulator, there was placed a silica-alumina carrier having a diameter of 4.5 to 5.0 mm. While the rotating dish was rotated at 15 rpm in a state tilted at 30° to the horizontal plane, 7.5 parts of ion-exchanged water as a liquid binder was sprayed over a period of 10 minutes. Then, the dried material (A) was added and supported on the carrier to obtain a supported material.

Next, the resultant supported material was removed and then calcined for 6 hours at 400° C. under air atmosphere to obtain a catalyst (1). The metal element composition of the catalyst (1) except for oxygen was shown below.

Catalyst (1): $Mo_{12}V_{5.8}W_{1.6}Cu_{2.6}$

The ignition loss ratio of the dried material (A) and the attrition loss and supporting ratio of the catalyst (1) are listed in Table 1.

(Oxidation Reaction)

The catalyst (1) (1000 mL) was filled into a stainless reaction tube of 25 mm in inner diameter. An oxidation reaction of acrolein was conducted by introducing a mixed gas including 4% by volume of acrolein, 5% by volume of oxygen, 40% by volume of water vapor and 51% by volume of nitrogen into the reaction tube at a space velocity of 1800 $hr^{-1}$ (STP). Results were listed in Table 1.

Examples 2 to 3

Preparation of Dried Materials and Production of Catalysts

Dried materials (B) and (C) were prepared in the same way as of Example 1, and then catalysts (2) and (3) were obtained in the same way as of Example 1 also in the production of catalysts, except that the temperature of 220° C. of heating the solid under air atmosphere, when preparing the dried materials, was changed to 190° C. and 150° C. respectively, and that the amount of the liquid binder being added was changed respectively as listed in Table 1. The metal element compositions except for oxygen of the catalysts (2) and (3) were the same as that of the catalyst (1).

The ignition loss ratios of the dried materials (B) and (C) and the attrition losses and supporting ratios of the catalysts (2) and (3) are listed in Table 1.

(Oxidation Reaction)

Oxidation reactions were carried out in the same way as of Example 1, except that the catalyst (2) and the catalyst (3) were used instead of the catalyst (1) in the oxidation reaction of Example 1. Results were listed in Table 1.

Comparative Examples 1 to 2

Preparation of Dried Materials and Production of Catalysts

Dried materials (D) and (E) were prepared in the same way as of Example 1, and then catalysts (c1) and (c2) were obtained in the same way as of Example 1 also in the production of catalysts, except that the temperature of 220° C. of heating the solid under air atmosphere, when preparing the dried materials, was changed to 400° C. and 250° C. respectively, and that the amount of the liquid binder being added was changed respectively as listed in Table 1. The metal element compositions except for oxygen of the catalysts (c1) and (c2) were the same as that of the catalyst (1).

The ignition loss ratios of the dried materials (D) and (E) and the attrition losses and supporting ratios of the catalysts (c1) and (c2) are listed in Table 1.

(Oxidation Reaction)

Oxidation reactions were carried out in the same way as of Example 1, except that the catalyst (c1) and the catalyst (c2) were used instead of the catalyst (1) in the oxidation reaction of Example 1. Results were listed in Table 1.

Example 4

Preparation of Dried Material

The same mixed liquid of starting materials as of Example 1 was sprayed to a drum dryer being heated with a steam of 476 kPa in pressure, thus obtaining a solid. In this step, the contacting period with the surface of the drum was 60 seconds.

Then, this solid was pulverized so as to have particle sizes of not more than 500 μm, thus obtaining a dried material (F).

(Production of Catalyst)

Onto a rotating dish of a dish type tumbling granulator, there was placed a silica-alumina carrier having a diameter of 4.5 to 5.0 mm. While the rotating dish was rotated at 15 rpm in a state tilted at 30° to the horizontal plane, 6.7 parts of ion-exchanged water as a liquid binder was sprayed over a period of 10 minutes. Then, the dried material (F) was added and supported on the carrier to obtain a supported material.

Next, the resultant supported material was removed and then calcined for 6 hours at 400° C. under air atmosphere to obtain a catalyst (4). The metal element composition except for oxygen of the catalyst (4) was the same as that of the catalyst (1).

The ignition loss ratio of the dried material (F) and the attrition loss and supporting ratio of the catalyst (4) are listed in Table 1.

(Oxidation Reaction)

An oxidation reaction was carried out in the same way as of Example 1, except that the catalyst (4) was used instead of the catalyst (1) in the oxidation reaction of Example 1. Results were listed in Table 1.

Example 5

Preparation of Dried Material and Production of Catalyst

Dried material (G) was prepared in the same way as of Example 4, and then catalyst (5) was obtained in the same way as of Example 4 also in the production of catalyst, except that the contacting period with the surface of the drum, when preparing the dried materials, was changed to 20 seconds, and that the amount of the liquid binder being added was changed as listed in Table 1. The metal element composition except for oxygen of the catalyst (5) was the same as that of the catalyst (1).

The ignition loss ratio of the dried material (G) and the attrition loss and supporting ratio of the catalyst (5) are listed in Table 1.

(Oxidation Reaction)

An oxidation reaction was carried out in the same way as of Example 1, except that the catalyst (5) was used instead of the catalyst (1) in the oxidation reaction of Example 1. Results were listed in Table 1.

Example 6

Preparation of Dried Material

Ammonium molybdate (3,000 parts), 994 parts of ammonium metavanadate, 574 parts of ammonium paratungstate and 500 parts of ammonium nitrate were dissolved into 20,000 parts of pure water under heating and mixing. Separately from this, 958 parts of copper nitrate trihydrate was dissolved into 2,000 parts of pure water under heating and mixing. The resultant two aqueous solutions were mixed together to obtain a mixed liquid of starting materials.

This mixed liquid of starting materials was sprayed to a drum dryer being heated with a steam of 476 kPa in pressure, thus obtaining a solid. In this step, the contacting period with the surface of the drum was 20 seconds.

Then, this solid was pulverized so as to have particle sizes of not more than 500 μm, thus obtaining a dried material (H).

(Production of Catalyst)

Onto a rotating dish of a dish type tumbling granulator, there was placed a silica-alumina carrier having a diameter of 4.5 to 5.0 mm. While the rotating dish was rotated at 15 rpm in a state tilted at 30° to the horizontal plane, 6.0 parts of ion-exchanged water as a liquid binder was sprayed over a period of 10 minutes. Then, the dried material (H) was added and supported on the carrier to obtain a supported material.

Next, the resultant supported material was removed and then calcined for 6 hours at 400° C. under air atmosphere to obtain a catalyst (6). The metal element composition of the catalyst (6) except for oxygen was shown below.

Catalyst (6): $Mo_{12}V_{5.8}W_{1.6}Cu_{2.6}$

The ignition loss ratio of the dried material (H) and the attrition loss and supporting ratio of the catalyst (6) are listed in Table 1.

(Oxidation Reaction)

An oxidation reaction was carried out in the same way as of Example 1, except that the catalyst (6) was used instead of the catalyst (1) in the oxidation reaction of Example 1. Results were listed in Table 1.

Examples 7 to 8

Preparation of Dried Materials and Production of Catalysts

Catalysts (7) and (8) were obtained in the same way as of Example 3 except that the amount of the liquid binder being added was changed respectively as listed in Table 1. The metal element compositions except for oxygen of the catalysts (7) and (8) were the same as that of the catalyst (1).

The ignition loss ratio of the dried material (C) and the attrition losses and supporting ratios of the catalysts (7) and (8) are listed in Table 1.

(Oxidation Reaction)

Oxidation reactions were carried out in the same way as of Example 1, except that the catalyst (7) and the catalyst (8) were used instead of the catalyst (1) in the oxidation reaction of Example 1. Results were listed in Table 1.

Comparative Example 3

Preparation of Dried Material

Dried material (I) was obtained in the same way as of Example 6, except that the pressure of the steam for heating the drum drier in the preparation of the dried material was changed to 270 kPa.

(Production of Catalyst)

Onto a rotating dish of a dish type tumbling granulator, there was placed a silica-alumina carrier having a diameter of 4.5 to 5.0 mm. While the rotating dish was rotated at 15 rpm in a state tilted at 30° to the horizontal plane, 6.0 parts of ion-exchanged water as a liquid binder was sprayed over a period of 10 minutes. Then, the dried material (I) was added to attempt to support it on the carrier. However, the resultant supported materials cohered to thus bunch up together on the way of the supporting operation. Therefore, the supporting operation was halted.

The ignition loss ratio of the dried material (1) is listed in Table 1.

Comparative Example 4

Preparation of Dried Material and Production of Catalyst

Catalyst (c3) was obtained by supporting the dried material (I) on the carrier to carry out the production of the catalyst in the same way as of Comparative Example 3, except that the amount of the liquid binder being added was changed as listed in Table 1. The metal element composition except for oxygen of the catalyst (c3) was the same as that of the catalyst (1).

The ignition loss ratio of the dried material (I) and the attrition loss and supporting ratio of the catalyst (c3) are listed in Table 1.

(Oxidation Reaction)

An oxidation reaction was carried out in the same way as of Example 1, except that the catalyst (c3) was used instead of the catalyst (1) in the oxidation reaction of Example 1. Results were listed in Table 1.

TABLE I

| | Catalyst | Dried material | Ignition loss ratio of dried material (% by mass) | Amount of binder added (parts by mass) | Supporting ratio of catalyst (% by mass) | Attrition loss of catalyst (% by mass) | Conversion of acrolein (% by mol) | Selectivity of acrylic acid (% by mol) | Yield of acrylic acid (% by mol) |
|---|---|---|---|---|---|---|---|---|---|
| Example 1 | (1) | (A) | 7.3 | 7.5 | 20.0 | 7.5 | 98.3 | 94.7 | 93.1 |
| Example 2 | (2) | (B) | 12.0 | 7.0 | 20.2 | 5.6 | 98.7 | 94.7 | 93.5 |
| Example 3 | (3) | (C) | 19.5 | 7.0 | 20.2 | 3.2 | 98.7 | 94.7 | 93.5 |
| Example 4 | (4) | (F) | 24.4 | 6.7 | 20.0 | 3.4 | 98.5 | 94.5 | 93.1 |
| Example 5 | (5) | (G) | 31.1 | 6.5 | 20.3 | 4.7 | 98.6 | 94.3 | 93.0 |
| Example 6 | (6) | (H) | 36.1 | 6.0 | 20.0 | 7.8 | 98.5 | 93.9 | 92.5 |
| Example 7 | (7) | (C) | 19.5 | 4.5 | 20.0 | 6.2 | 98.3 | 94.3 | 92.7 |
| Example 8 | (8) | (C) | 19.5 | 15.0 | 20.0 | 4.2 | 98.7 | 94.2 | 93.0 |
| Comparative Example 1 | (c1) | (D) | 0.0 | 8.0 | 20.2 | 18.2 | 94.0 | 95.7 | 90.0 |
| Comparative Example 2 | (c2) | (E) | 3.9 | 8.0 | 20.1 | 15.4 | 96.2 | 94.1 | 90.5 |
| Comparative Example 3 | — | (I) | 41.1 | 6.0 | — | — | — | — | — |
| Comparative Example 4 | (c3) | (I) | 41.1 | 3.0 | 19.9 | 12.3 | 97.0 | 94.4 | 91.6 |

What is claimed is:

1. A process for the production of acrylic acid comprising the steps of:
   a) drying a batch of a mixed liquid of starting materials including molybdenum and vanadium as essential components to give a dried material, wherein the step of drying said mixed liquid comprises the step of heating said mixed liquid at a temperature of not more than 230° C. for a heating period of less than 90 minutes;
   b) testing a portion of said dried material to determine whether an ignition loss ratio of said dried material is from 5 to 40% by mass;
   c) molding, after said step of testing, a portion of said dried material having an ignition loss ratio from 5 to 40% by mass with a liquid binder;
   d) calcining the resultant molding to produce a catalyst; and
   e) subjecting acrolein to a catalytic gas phase oxidation employing said catalyst in the presence of molecular oxygen to produce acrylic acid;
   with the proviso that the ignition loss ratio of the dried material is calculated according to the following formula based on masses of the dried material before and after heated, the dried material being heated until there is no mass change at 300° C. under air atmosphere:

ignition loss ratio(% by mass)=[(mass of dried material before heated($g$)−mass of dried material after heated($g$))/mass of dried material before heated ($g$)]×100.

2. The process of claim 1, wherein the liquid binder comprises water as an essential component, and is used in an amount of 2 to 20 parts by mass in terms of water relative to 100 parts by mass of the dried material.

3. The process of claim 1, wherein the step of molding includes supporting said dried material on a particulate carrier.

4. The process of claim 2, wherein the step of molding includes supporting said dried material on a particulate carrier.

5. The process of claim 1, wherein said step of calcining the resultant molding comprises the step of calcining the resultant molding at a temperature of 350 to 450° C.

6. The process of claim 1 and further comprising the step of adjusting the ignition loss ratio of said dried material, with the step of adjusting occurring after the step of testing and prior to the step of molding.

7. A process for the production of acrylic acid comprising the steps of:
   a) drying a batch of a mixed liquid of starting materials including molybdenum and vanadium as essential components to give a dried material, wherein the step of drying said mixed liquid comprises the step of heating said mixed liquid at a temperature of not more than 230° C. for a heating period of less than 90 minutes;
   b) testing a portion of said dried material to determine whether an ignition loss ratio of said dried material is from 5 to 40% by mass;
   c) molding, after said step of testing, a portion of said dried material having an ignition loss ratio from 5 to 40% by mass with a liquid binder;
   d) calcining the resultant molding to produce a catalyst, wherein an attrition loss of the catalyst is less than 10% by mass; and
   e) subjecting acrolein to a catalytic gas phase oxidation employing said catalyst in the presence of molecular oxygen to produce acrylic acid;
   with the proviso that the ignition loss ratio of the dried material is calculated according to the following formula based on masses of the dried material before and after heated, the dried material being heated until there is no mass change at 300° C. under air atmosphere:

ignition loss ratio(% by mass)=[(mass of dried material before heated($g$)−mass of dried material after heated($g$))/mass of dried material before heated ($g$)]×100;

with the proviso that the attrition loss is calculated according to the following formula based on a mass (g) of the resultant catalyst for production of acrylic acid initially charged into a stainless airtight vessel, which is in the form of a cylindrical drum of 150 mm diameter of circular section in perpendicular direction and 150 mm width in horizontal direction, and a mass (g) of the catalyst remaining on a 2.0 mm-mesh sieve after subjected to an operation comprising the steps of weighing out 200±1 g of the catalyst precisely, charging the weighed catalyst into the stainless airtight vessel, rotating the vessel for 30 minutes at 150 rpm around a horizontal central axis thereof, and then putting the catalyst through the sieve:

attrition loss(% by mass)=[(mass of catalyst initially charged into vessel(g)−mass of catalyst remaining on sieve(g))/mass of catalyst initially charged into vessel(g)]×100.

8. The process of claim 7, wherein the liquid binder comprises water as an essential component, and is used in an amount of 2 to 20 parts by mass in terms of water relative to 100 parts by mass of the dried material.

9. The process of claim 7, wherein the step of molding includes supporting said dried material on a particulate carrier.

10. The process of claim 8, wherein the step of molding includes supporting said dried material on a particulate carrier.

11. The process of claim 7, wherein said step of calcining the resultant molding comprises the step of calcining the resultant molding at a temperature of 350 to 450° C.

12. The process of claim 6, wherein the step of adjusting comprises, when the ignition loss ratio of the dried material is above 40% by mass, the step of changing conditions of said step of heating.

\* \* \* \* \*